United States Patent
Higashida et al.

(10) Patent No.: US 6,878,277 B2
(45) Date of Patent: Apr. 12, 2005

(54) PHOTOCATALYTIC FILTER, PHOTOCATALYTIC FILTER DEVICE AND METHOD FOR MANUFACTURING PHOTOCATALYTIC FILTER

(75) Inventors: Masayuki Higashida, Tokyo (JP); Yoshikazu Nishii, Gunma-ken (JP); Kazuya Uchida, Tokyo (JP)

(73) Assignees: Hoya Candeo Optronics Corporation, Toda (JP); Hoya Corporation, Tokyo (JP)

( * ) Notice: Subject to any disclaimer, the term of this patent is extended or adjusted under 35 U.S.C. 154(b) by 212 days.

(21) Appl. No.: 10/175,281

(22) Filed: Jun. 20, 2002

(65) Prior Publication Data

US 2002/0195381 A1 Dec. 26, 2002

(30) Foreign Application Priority Data

Jun. 20, 2001 (JP) .................................... 2001-186955

(51) Int. Cl.⁷ .............................................. B01D 71/04
(52) U.S. Cl. ............ 210/500.26; 210/490; 210/497.01; 210/504; 210/509; 156/60; 55/512; 55/514; 501/37

(58) Field of Search ................. 55/512, 514, 524, 55/527; 156/60, 73.6, 219–221; 210/490, 491, 497.01, 500.26, 504, 509, 497.1; 252/520.22, 521.3; 422/312; 501/32, 37–39, 53–55; 502/5

(56) References Cited

U.S. PATENT DOCUMENTS 6,468,428 B1 * 10/2002 Nishii et al. ............. 210/497.3
6,764,655 B1 *  7/2004 Nishii et al. ............. 422/122

FOREIGN PATENT DOCUMENTS

| JP | 10-118415 A | 5/1988 |
| JP | 9-225262 A | 9/1997 |
| JP | 2000-5691 A | 1/2000 |
| JP | 2001-009292 A1 * | 1/2001 |
| WO | WO 97/31703 * | 9/1997 |

* cited by examiner

Primary Examiner—W. L. Walker
Assistant Examiner—Krishnan S Menon
(74) Attorney, Agent, or Firm—Nixon & Vanderhye P.C.

(57) ABSTRACT

Disclosed is a photocatalytic filter which can fully secure a space of gaps to constitute a flow path for flowing a fluid to be disposed of and which has gaps structured for easily trapping an organic substance in the fluid when the fluid is brought into contact with a photocatalyst layer.

5 Claims, 8 Drawing Sheets

PHOTOCATALYTIC FILTER, PHOTOCATALYTIC FILTER DEVICE AND METHOD FOR MANUFACTURING PHOTOCATALYTIC FILTER

This application claims priority over the Japanese application JP 2001-186955 of 06/20/2001.

BACKGROUND OF THE INVENTION

The present invention relates to a photocatalytic filter, a photocatalytic filter device to which the photocatalytic filter is applied, and a method for manufacturing a photocatalytic filter.

A photocatalyst is a material that exhibits functions of sterilization, antimicrobial activity, decomposition, deodorization, non-soiling, non-fogging, and the like when exposed to light. When titanium dioxide, a typical example of the photocatalyst, is exposed to light, the titanium dioxide causes an intense redox reaction on its surface to decompose a substance that is in contact with the surface. For example, when the above substance is an organic substance, the organic substance is decomposed into carbon dioxide gas and water. The photocatalyst decomposes, for example, environmental pollutants such as dioxin and trichloroethylene and volatile organic compounds that may cause a sick building syndrome to make them harmless.

Attempts are being made to utilize the above photocatalysis for a filter and apply the filter to disposing of various liquids, disposing of various gases and environmental cleaning.

As a photocatalytic filter that is developed to provide a high-performance photocatalytic filter at a less expensive price, there is proposed a photocatalytic filter using a bundle of photocatalytic filter materials (JP-A-9-225262 and JP-A-10-118415). The above bundle of photocatalytic filter materials is formed by uniformly distributing particles on an outer surface of each of photoconductive filaments (including light transmissive filaments and light guiding filaments), bonding the particles to the outer surface, forming a photocatalyst layer on the outer surfaces of the particles and the remaining outer surface of each filament to produce many photocatalytic filter materials, and bundling these many photocatalytic filter materials such that the forward and backward ends of each photocatalytic filter material are respectively aligned with such ends of other photocatalyst filter materials.

In the above photocatalytic filter, gaps are formed between neighboring photocatalytic filter materials due to the presence of the above particles, so that a fluid to be disposed of is flowed through the gaps to dispose of the fluid.

In the above photocatalytic filter, one end or each end of the bundle of a number of the photocatalytic filter materials is provided with a light incidence portion, and light such as ultraviolet ray is allowed to enter the light incidence portion (s) and propagated inside the photocatalytic filter materials. Since the photocatalyst layers have a higher refractive index (e.g., titanium dioxide; 2.1–2.6) than the filaments (e.g., glass fiber; about 1.5), the above propagated light leaks into the photocatalyst layer without causing total reflection, and the photocatalyst layers are irradiated with the leaked light.

And, a fluid to be disposed of is allowed to flow through gaps formed among the photocatalytic filter materials, and in a state where an organic substance contained in the fluid is in contact with the photocatalyst layers, the photocatalyst layers are irradiated with the above leaked light, so that the organic substance that comes in contact with the photocatalyst layers is decomposed by photocatalysis and removed.

Meanwhile, filaments having numerous particles uniformly distributed on the outer surface thereof are bundled. In this case, the particles that constitute bases for forming gaps are required to have a relatively large diameter for accomplishing the purpose of securing a flow space sufficient for flowing a fluid to be disposed of.

However, linear materials or filaments having a diameter of approximately 70 to 200 $\mu$m are preferably used as such, and for bonding numerous particles to outer surfaces of the filaments having such a small diameter, it is desirable to use particles of which the diameter is as small as possible. For example, when one particle is bonded to a surface of a filament having a diameter of 125 $\mu$m, properly, the diameter of the particle is approximately 10 $\mu$m for securing sufficient adhesion.

When numerous particles having such a very small diameter (approximately 10 $\mu$m) are bonded to outer surfaces of the filaments to form a uniform distribution of the particles, it is impossible to overcome the above problem (the requirement to form gaps that secure a sufficient space for flowing a fluid to be disposed of). It is alternatively expected that a spacer having a certain thickness is interposed between one filament and another filament. However, it is impossible to interpose such a spacer among the filaments having a very small diameter in essence.

A photocatalytic filter is conventionally required to secure gaps formed among photocatalytic filter materials that are bundled, as a flow space for flowing a fluid to be disposed of. However, no conventional photocatalytic filters can comply with the above requirement. Further, it is conventionally required to form a gap structure suitable for trapping an organic substance of the fluid that is brought into contact with a photocatalyst layer. Again, however, no conventional photocatalytic filters can comply with the above requirement.

A conventional photocatalytic filter is constituted of a number of photocatalytic filter materials that are bundled, and it is conventionally required to develop a method having improved productivity in the step of bonding particles to filter materials. However, such a method has not yet been developed.

SUMMARY OF THE INVENTION

The present invention has been made under the above background, and it is a first object of the present invention to provide a photocatalytic filter which can fully secure a space of gaps to constitute a flow path for flowing a fluid to be disposed of and which has gaps structured for easily trapping an organic substance in a fluid to be disposed of when the fluid is brought into contact with a photocatalyst layer.

It is a second object of the present invention to provide a photocatalytic filter device to which the above photocatalytic filter is applied.

It is a third object of the present invention to provide a method for manufacturing a photocatalytic filter that is improved in productivity in the step of bonding particles to filter materials.

It is a fourth object of the present invention to provide a method of bonding particles to the outer surface of each of a number of linear materials or filaments.

For achieving the above first object of the present invention, the photocatalytic filter of the present invention comprises a bundle of photocatalytic filter material, each photocatalytic filer material being formed of photoconductive particles, a photoconductive linear material and a photocatalyst layer, the particles being bonded to an outer surface of the linear material, the photocatalyst layer being formed on an outer surface of the linear material to which the particles are bonded, and on outer surfaces of the particles, the photocatalytic filter materials being bundled for flowing a fluid to be disposed of, through gaps formed among said photocatalytic filter materials that are neighboring to one another, to dispose of the fluid, said particles having a diameter smaller than the diameter of said linear materials, being bonded to the outer surface of each linear material and forming stacks which have a plurality of stages each and are in the form of islands on the outer surface of each linear material.

The photocatalytic filter device of the present invention relates to a photocatalytic filter device to which the above photocatalytic filter is applied.

For achieving the above second object of the present invention, the photocatalytic filter device comprises the above photocatalytic filter and a filter case, the photocatalytic filter being housed in the filter case, the filter case having a flange portion on one side of the filter case and other flange portion on the other side, the flange portion on one side having a side portion provided with an inlet port for introducing the above fluid to be disposed of, the flange portion on the other side having a side portion provided with an outlet port for discharging said fluid disposed of, one or each of the flange portions having a front side provided with a window for allowing light to enter a light incidence portion of said photocatalytic filter.

The method for manufacturing a photocatalytic filter, provided by the present invention, relates to a method for manufacturing the above photocatalytic filter.

For achieving the above third object of the present invention, the method comprises the steps of:

providing a predetermined number of photoconductive linear materials and a predetermined number of particles, and bonding said particles to surfaces of said linear materials and forming a photocatalyst layer on each of the linear materials to which the particles are bonded, the bonding step comprising the sub-steps of:

temporarily bonding said particles to said linear materials while an adhesive liquid is interposed between the linear materials and the particles, and drying or curing said adhesive liquid while said linear materials are moved in a relative motion by applying accelerated motion based on shaking or rocking to said linear materials to which the particles are temporarily bonded.

For achieving the above fourth object of the present invention, the method of bonding particles to outer surfaces of a number of linear materials, comprises the steps of:

forming a mixture of a number of said linear materials, the particles and an adhesive liquid where the particles in a large mount are present among said linear materials, and the adhesive liquid is present between the linear materials and the particles, to temporarily bond the particles to the linear materials, and drying or curing said adhesive liquid while applying an accelerated motion based on shaking or rocking the mixture to the mixture to move said linear materials relatively to one another.

DETAILED DESCRIPTION OF THE INVENTION

In the above photocatalytic filter of the present invention, preferably, the above "photoconductive linear material" has the form of a fiber, and the above "photoconductive particles" have the form of a sphere, and the material for each of these is a glass or a plastic. In the present specification including claims, the term "photoconductive" means not only "photoconductive" in narrower sense but also "light transmissive" and "light guiding".

The above "linear material" properly has a diameter in the range of from 50 to 300 μm, preferably, 70 to 200 μm, and a length in the range of from 30 to 500 mm.

The above "particles" properly have an average diameter in the range of from 1 to 100 μm, and the average diameter of the particles is determined to be smaller than the diameter of the linear material.

The material for the above "photocatalyst layer" includes titanium dioxide as a typical example, and it can be also selected from barium titanate, strontium titanate, sodium titanate, zirconium dioxide, cadmium sulfide or $\alpha$-$Fe_2O_3$. The photocatalyst layer properly has a thickness of approximately 0.1 to 10 μm.

The method of forming the above photocatalyst layer includes a dipping method in which the linear materials are dipped in a photocatalyst in the form of a liquid and lifted at a predetermined speed to form a photocatalyst layer having a predetermined thickness on the surface of the linear material, and a blow-away method in which the linear materials are immersed in a photocatalyst in the form of a liquid, then extra liquid is removed by a predetermined gas current and the photocatalyst is dried (JP-A-2000-5691).

In the method for manufacturing a photocatalytic filter, provided by the present invention, the above sub-step of temporary bonding specifically includes temporarily bonding a predetermined number of quartz glass spheres to each of a predetermined number of glass fibers through (with) an adhesive liquid. As a state of the above temporary bonding, preferably, there can be maintained a state in which, when quartz glass spheres are sandwiched between glass fibers and the glass fibers are one another aligned in both ends, bundled and lifted up, almost no quartz glass spheres fall off the bundle of the glass fibers.

In the above case in the sub-step of temporary bonding, an adhesive liquid is allowed to be present in the bundle of the glass fibers, and the quartz glass spheres are incorporated. In this case, preferably, the quartz glass spheres and the adhesive liquid are uniformly mixed among the glass fibers.

In the above case in the sub-step of temporary bonding, there may be employed a method in which the glass fibers and the quartz glass spheres are mixed in advance and the adhesive liquid is allowed to infiltrate into gaps between the glass fibers and the quartz glass spheres.

In the sub-step of curing the adhesive liquid refers to a step in which, in the above case, the applied adhesive liquid is dried or cured while an accelerated motion such as shaking or rocking is applied to a predetermined number of the glass fibers to which a predetermined number of the quartz glass spheres are bonded, to move the glass fibers relatively to one another in a relative motion (in other words, while different motions are applied to the glass fibers to move them in different motions).

In the above sub-step of curing the adhesive liquid, the glass fibers having a larger diameter are overwhelmingly greater in mass than the quartz glass spheres having a smaller diameter, so that the bonding strength between the glass fiber and the quartz glass sphere is greater than the bonding strength between the quartz glass spheres themselves.

In the above sub-step of curing the adhesive liquid, therefore, the glass fibers are moved relatively to one another in a relative motion as described already, whereby the glass fibers can be released from their temporary bonding state and isolated from one another. The adhesive liquid is dried or cured in a state where the quartz glass spheres are bonded to the glass fibers having higher bonding strength, so that all the glass fibers are isolated from one another, whereby there are produced individual glass fibers each of which has a surface to which a predetermined number of the quartz glass spheres are bonded with the adhesive.

In the photocatalytic filter of the present invention, the particles constituting bases for forming filter gaps (flow paths) through which to flow a fluid to be disposed of, are bonded to the outer surface of each linear material and form stacks which have a plurality of stages each and are present in the form of islands or aggregates, so that gaps sufficient for flowing the fluid to be disposed of can be formed and that an internal structure for easily trapping the substance to be disposed of can be constituted. Further, adhesion areas between the particles and the linear materials increase, adhesion strength increases, and far stronger bonding can be attained. When such linear materials are bundled, gaps formed between one linear material and another liner material do not easily change with the passage of time and are stabilized.

In the photocatalytic filter of the present invention, the amount of the particles between one linear material and another linear material can be increased for increasing the number of stages of each stack of the particles, and the above amount of the particles can be decreased for decreasing the number of stages of each stack of the particles.

In the method for manufacturing a photocatalytic filter, provided by the present invention, the number of stages of each stack of the particles can be decreased when the amount of the rocking motion (width, velocity and frequency of rocking motion) is increased. Further, with regard to rocking conditions, drying conditions (temperature of hot air, air flow, time period, etc.), these conditions are classified into parameters and the parameters are mechanically controlled, whereby reproductive conditions can be easily produced. In this manner, there can be mass-produced photocatalytic filter materials each having a surface to which the small-diameter particles that are stacked in a plurality of stages and in the form of islands or aggregates are bonded and fixed.

PREFERRED EMBODIMENTS OF THE INVENTION

Example 1

Figure 1:
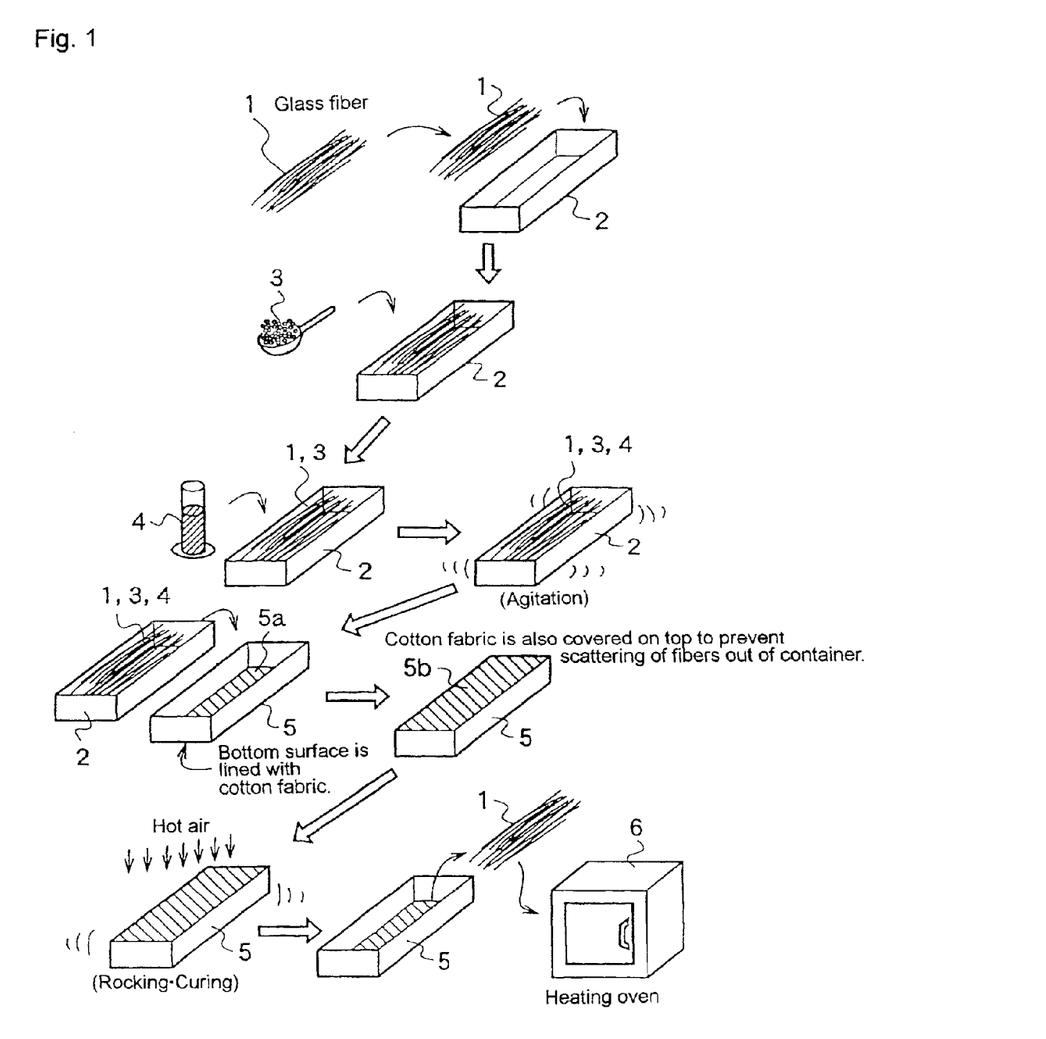
FIG. 1 is a drawing for explaining Example 1 directed to the method for manufacturing a photocatalytic filter, provided by the present invention.

FIG. 1 shows a method for manufacturing a photocatalytic filter, provided by the present invention, in Example 1. The method comprises (1) the sub-step of temporary bonding, (2) the sub-step of curing an adhesive liquid and (3) the step of forming photocatalytic filter materials. These steps will be explained in detail below.

(1) Sub-Step of Temporary Bonding

As shown in FIG. 1, there are provided as linear materials 6,000 glass fibers 1 which have a diameter of 125 $\mu$m and a length of 260 mm each and are made of quartz (or "PFG1 Glass Fibers", trade name, supplied by HOYA CORPORATION). The glass fibers 1 are aligned in their longitudinal direction, and all of them (6,000 glass fibers) are placed in a proper container 2 (for example, "Natural Pack N-10", trade name, supplied by K.K. Nishiyama Kagaku, dimensions of 80×60×280 mm).

Further, as particles, there are provided 40 g of quartz glass spheres 3 having an average particle diameter of 50 $\mu$m ("SSV-43", trade name, supplied by K.K. Tatsumori), and the quartz glass spheres are placed in the above container 2.

Then, 40 milliliters of an adhesive liquid 4 ("FJ-803", trade name, supplied by Tokiwa Denki K.K.) is placed in the above container 2 with the glass fibers 1 and the quartz glass spheres 3 in it, and the container 2 is closed with a lid. The container 2 is reciprocally moved (stroke 80 mm, 5 strokes/second), to obtain a state in which a predetermined number of the quartz glass spheres 3 adhere to surfaces of a number of the glass fibers 1 with the adhesive liquid 4 to attain temporary bonding of the glass fibers 1 and the quartz glass spheres 3. The above "predetermined number of quartz glass spheres" is determined depending upon the amount of the quartz glass spheres 3 (40 g), the volume of the glass fibers 1, the volume of the container 2, the amount of the adhesive liquid 4, and the like.

(2) Sub-Step of Curing Adhesive Liquid

The glass fibers 1 to which the quartz glass spheres 3 are temporarily bonded are housed in a dry container 5 (dimensions of 200×80×300 mm). The bottom and top of the dry container 5 are covered with cotton fabrics 5a and 5b, the above glass fibers 1 are placed on the cotton fabric 5a, and the cotton fabric 5b constitutes a lid of the dry container 5.

Then, the above dry container 5 with the glass fibers 1 in it is rocked or shaken. The rocking or shaking is carried out by reciprocal motion of 4 strokes/second at a stroke of 100 mm, such that the glass fibers 1 move in an accelerated motion independently of one another at right angles with the longitudinal direction of the glass fibers 1. At the same time, hot air (80° C.) is blown through the cotton fabric 5a or 5b for drying the applied adhesive liquid 4.

By the above procedures, the glass fibers 1 are isolated from one another and are blown with the hot air in a state where a predetermined number of the quartz glass spheres 3 are bonded to the surface of each glass fiber 1, and the applied adhesive liquid is accordingly dried and cured, to give glass fibers 1 (total amount: 6,000 glass fibers) to which a predetermined number of the quartz glass spheres 3 are bonded and fixed. The rocking and the blowing with hot air are carried out for approximately 10 minutes until the applied adhesive liquid is completely dried.

Then, the above glass fibers 1 are taken out of the container 5, placed in a heating oven 6 and heat-treated (300° C., 2 hours) for further enhancing the adhesion strength.

By the above procedures, there are obtained filter materials for photocatalysis, in which a predetermined number of the quartz glass spheres 3 are bonded to surfaces of the glass fibers 1.

Figure 2:
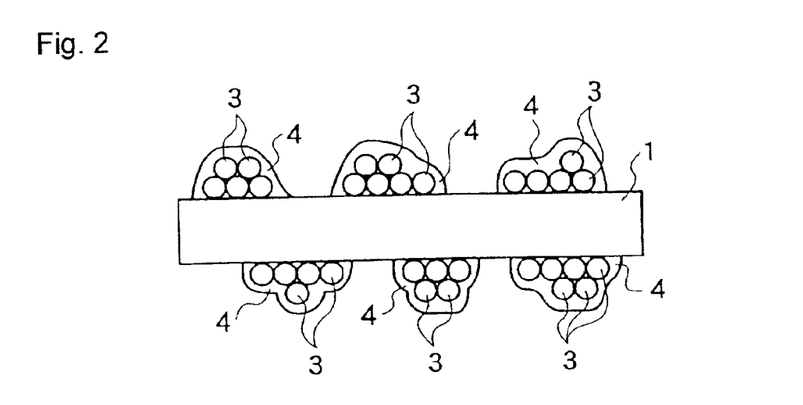
FIG. 2 is a drawing for showing a filter material for a photocatalyst in the present invention.

In each of the above filter materials, the quartz glass spheres 3 are bonded and fixed to the surface of the glass fiber 1 with an adhesive 4, as shown in FIG. 2, in a state where the quartz glass spheres 3 constitute stacks having a plurality of stages each and aggregates (stacks) of the quartz glass spheres are distributed in the form of islands.

Figure 3:
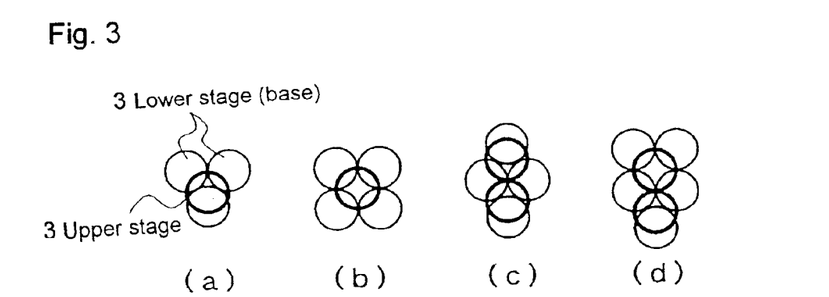
FIG. 3 is a drawing for showing embodiments of stacks of quartz glass spheres.

FIG. 3 shows embodiments of stacks of the quartz glass spheres 3. As shown in FIG. 3, the stack of the quartz glass spheres 3 consists of quartz glass spheres 3 forming a lower stage (base) on the glass fiber 1 and quartz glass sphere(s) 3 forming an upper stage stacked on the lower stage of the quartz glass spheres 3 on the glass fiber 1. In these embodiments, FIG. 3(a) shows a stack formed of a lower stage of three spheres and an upper stage of one sphere, FIG. 3(b) shows a stack formed of a lower stage of four spheres and an upper stage of one sphere, FIG. 3(c) shows a stack formed of a lower stage of four spheres and an upper stage of two spheres, and FIG. 3(d) shows a stack formed of a lower stage of five spheres and an upper stage of two spheres.

(3) Step of Forming Photocatalytic Filter

Figure 4:
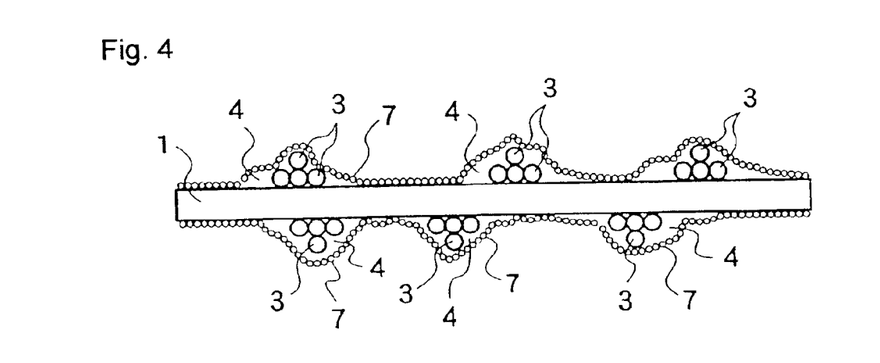
FIG. 4 is a drawing for showing a photocatalytic filter material in which a titanium dioxide layer is formed on an outer surface of a glass fiber.

In the glass fibers 1 obtained by the above sub-step of curing the adhesive liquid, a titanium dioxide ($TiO_2$) layer 7 as a photocatalyst is formed on the surface of each glass fiber 1 by a dipping method, to obtain photocatalytic filter materials. FIG. 4 shows a photocatalytic filter material having a titanium dioxide layer 7 (thickness: 2 $\mu$m), which is formed on surfaces by application. In the photocatalytic filter material, the titanium dioxide layer 7 is formed on surfaces of the quartz glass spheres 3 that are bonded and fixed with the adhesive 4 and form stacks of a plurality of stages in the form of islands or aggregates, and it is formed on that surface of the glass fiber 1 which are not covered with the bonding quartz glass spheres 3.

And, both ends of the above photocatalytic filter materials (total: 6,000 glass fibers) are aligned, and the photocatalytic filter materials are bundled to form a photocatalytic filter bundle, whereby a photocatalytic filter is completed.

In the above photocatalytic filter, the glass fibers 1 have sufficient gaps between one glass fiber and another glass fiber as the quartz glass spheres 3 bonded with an adhesive form stacks having a plurality of stages each. In the photocatalytic filter material shown in FIG. 4, the quartz glass spheres 3 forming lower stages occupy approximately 60% of the entire surface of the glass fiber 1 and the quartz glass spheres 3 forming upper stages occupy approximately 20% thereof. It should be noted that FIG. 4 shows one cross section taken by cutting the glass fiber 1 on a central axis thereof and that quartz glass spheres forming lower stages and upper stages occupy other areas of the glass fiber 1 which are not shown.

As described already, a photocatalyst layer 7 is formed on the surface of the glass fiber 1 having surface areas occupied by the quartz glass spheres 3, and a number of thus-produced photocatalytic filter materials are bundled to produce a photocatalytic filter. When the thus-produced photocatalytic filter was placed in a vessel containing a certain amount of water and measured for an amount of water that entered gaps among the photocatalytic filter materials to determine a porosity of the photocatalytic filter, the photocatalytic filter showed a porosity of approximately 60% and it was accordingly found that the space formed by the gaps was sufficient as a space for flowing a fluid to be disposed of.

According to the above Example 1, a predetermined number of the quartz glass spheres 3 having an average particle diameter of 50 $\mu$m can be bonded and fixed to each of the glass fibers 1 simultaneously by a simple step of blowing hot air while rocking or shaking the glass fibers 1 to which the quartz glass spheres 3 are temporarily bonded. Further, there is almost no risk of a strong force exerting on the glass fibers 1 and the like, so that the glass fibers 1 can be handled without any risk of breaking the glass fibers 1, etc., to attain high yields.

Figure 5:
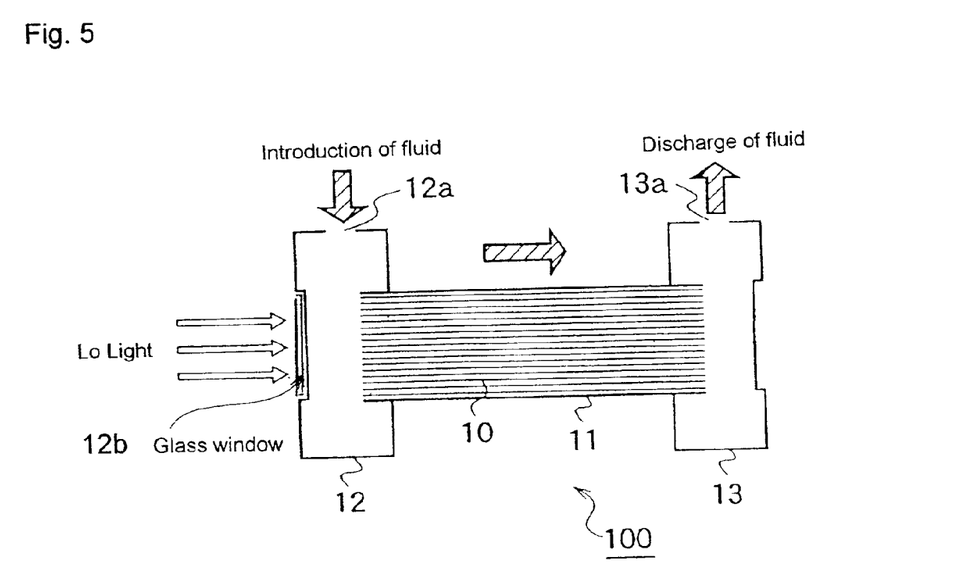
FIG. 5 is a drawing for showing a photocatalytic filter device to which the photocatalytic filter of the present invention is applied.

FIG. 5 shows a constitution of a photocatalytic filter device 100 to which the above photocatalytic filter indicated by numeral 10 is applied. As shown in FIG. 5, the photocatalytic filter device 100 has the above photocatalytic filter 10 housed in a filter case 11. The filter case 11 is provided with flange portions 12 and 13 formed on both sides thereof. The flange portion 12 has a side portion provided with a fluid inlet port 12a, and the flange portion 12 has a front side provided with a glass window 12b for the incidence of light $L_0$ such as ultraviolet ray. The flange portion 13 has a side portion provided with a fluid outlet port 13a.

In the thus-constituted photocatalytic filter device, a fluid to be disposed of is introduced through the fluid inlet port 12a and flows in a space formed among the photocatalytic filter materials constituting the photocatalytic filter 10, and an organic substance in the fluid is accordingly brought into contact with titanium dioxide layers formed on the outer surfaces of the photocatalytic filter materials and thereby trapped.

Light $L_0$ enters an incidence portion on one side of each of the photocatalytic filter materials constituting the photocatalytic filter 10 through the glass window 12b, and the light $L_0$ is propagated inside each photocatalytic filter material and leaks into each photocatalyst layer to irradiate each photocatalyst layer, whereby the above-trapped organic substance is decomposed by photocatalysis and removed.

In the above Example 1, the step of curing the adhesive liquid and the step of forming the photocatalyst layer are provided separately. However, these steps can be integrated by employing an adhesive having a photocatalytic effect.

Example 2

Figure 6:
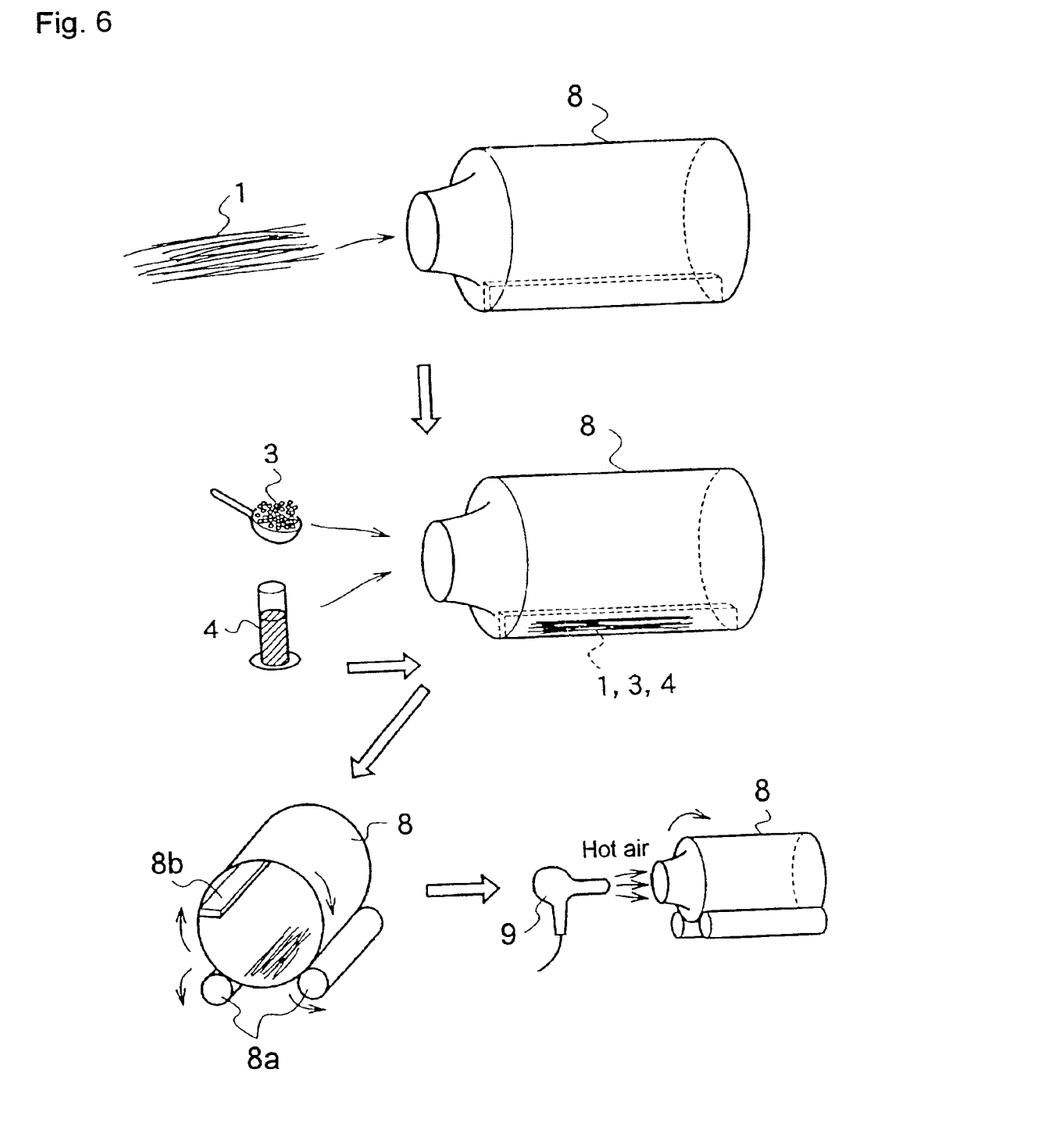
FIG. 6 is a drawing for explaining Example 2 directed to the method for manufacturing a photocatalytic filter, provided by the present invention.

FIG. 6 shows a method for manufacturing a photocatalytic filter, provided by the present invention. The procedure of Example 2 is the same as that of Example 1 except that a drum-shaped container 8 alone is used in the sub-steps of temporary bonding and curing an adhesive liquid. Example 2 will be therefore explained by addressing differences of Example 2 from Example 1.

(1) Sub-Step of Temporary Bonding

Glass fibers 1 (600 glass fibers), quartz glass spheres 3 (50 g) and an adhesive liquid 4 (40 ml) are charged into a drum-shaped container 8 (diameter 210 mm, length 300 mm) horizontally placed as shown in FIG. 6. Since the volume of the drumshaped container 8 is overwhelmingly large as compared with the total volume of the above glass fibers 1 (600 glass fibers), quartz glass spheres 3 (50 g) and adhesive liquid 4 (40 ml), the glass fibers 1, and the like are contained in a state where they are laid flat on a bottom-forming internal wall of the drum-shaped container 8.

(2) Sub-Step of Curing Adhesive Liquid Then, the drum-shaped container 8 is placed on rotary rollers 8a and 8a and driven to rotate (rotation speed: approximately 60 RPM). In an upper and internal circumferential portion of the drum-shaped container 8, there is provided a scratching bar 8b which is externally fixed with a fixing mechanism (not shown).

The glass fibers 1, and the like that are laid on the wall move upward along the wall of the drum-shaped container 8 due to the rotation of the drum-shaped container 8. However, they are blocked with the scratching bar 8b to come downward. In this manner, the glass fibers 1, and the like are agitated, and an impact exerts an accelerated motion on the glass fibers 1 to provide the glass fibers 1 with proper relative motions.

Then, while the drum-shaped container 8 is rotated, hot air is blown into the drum-shaped container 8 with a blower 9 for approximately 20 minutes to dry and cure the adhesive liquid 4, whereby a predetermined number of the quartz glass spheres 3 are bonded and fixed to the surface of each of the glass fibers 1.

Then, the above glass fibers 1 are taken out of the container 8, placed in a heating oven 6 and heat-treated (300° C., 2 hours) for further enhancing the adhesion strength in the same manner as in Example 1, whereby there are obtained photocatalytic filter materials in which a pre-determined number of the quartz glass spheres 3 are bonded to the surface of each glass fibers 1.

According to the above Example 2, there can be employed steps far simpler than those in Example 1, and filter materials can be mass-produced more rapidly.

Evaluation of Photocatalytic Filter Device

Figure 7:
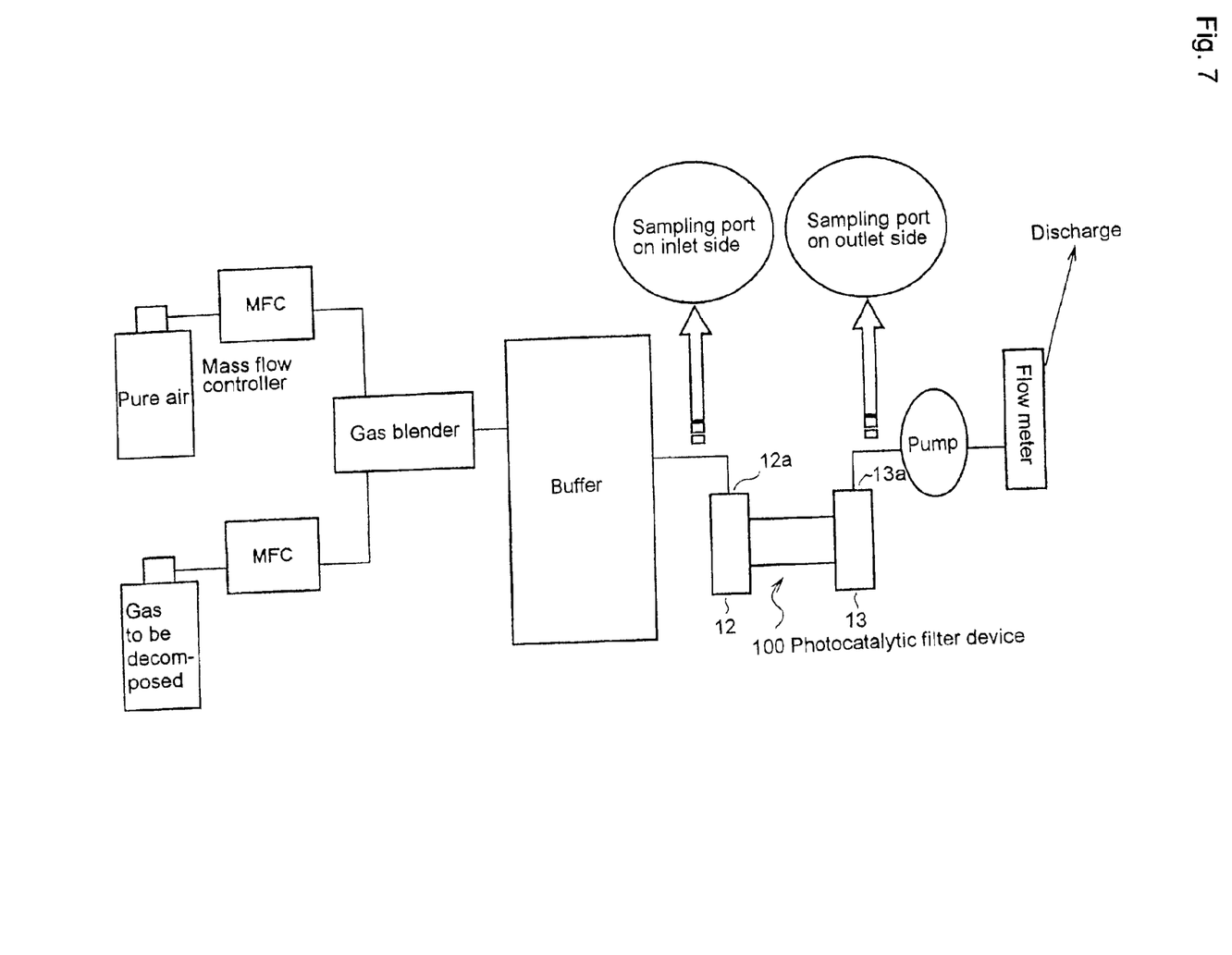
FIG. 7 is a drawing for showing the constitution of a system for conducting a performance test of a photocatalytic filter device.

For evaluating the photocatalytic filter device 100 shown in FIG. 5, a photocatalytic filter device performance testing system shown in FIG. 7 was employed.

The performance testing system is outlined as follows. First, pure air and gas to be decomposed are flowed at constant rates through mass flow controllers MFC and introduced into a gas blender. In the gas blender, gas to be decomposed is diluted with pure air to produce gas having a predetermined concentration.

Then, the above-produced gas is once stored in a buffer tank and then introduced to the fluid inlet port 12a of a photocatalytic filter device 100 of the present invention. The photocatalytic filter device 100 has an inlet side sampling port on the inlet side and an outlet side sampling port on the outlet side for detecting gas concentrations. Gas chromatographs are connected to these sampling ports as detectors.

The intensity of ultraviolet ray (365 nm) to enter the photocatalytic filter is set at 10 mw/cm$^2$, the gas to flow through the photocatalytic filter is adjusted to have a residence time of 2.7 seconds, and the flow rate of the gas is set at 2 liters/minute, to measure the photocatalytic filter for capability of decomposing the object gas contained in the air.

Figure 8:
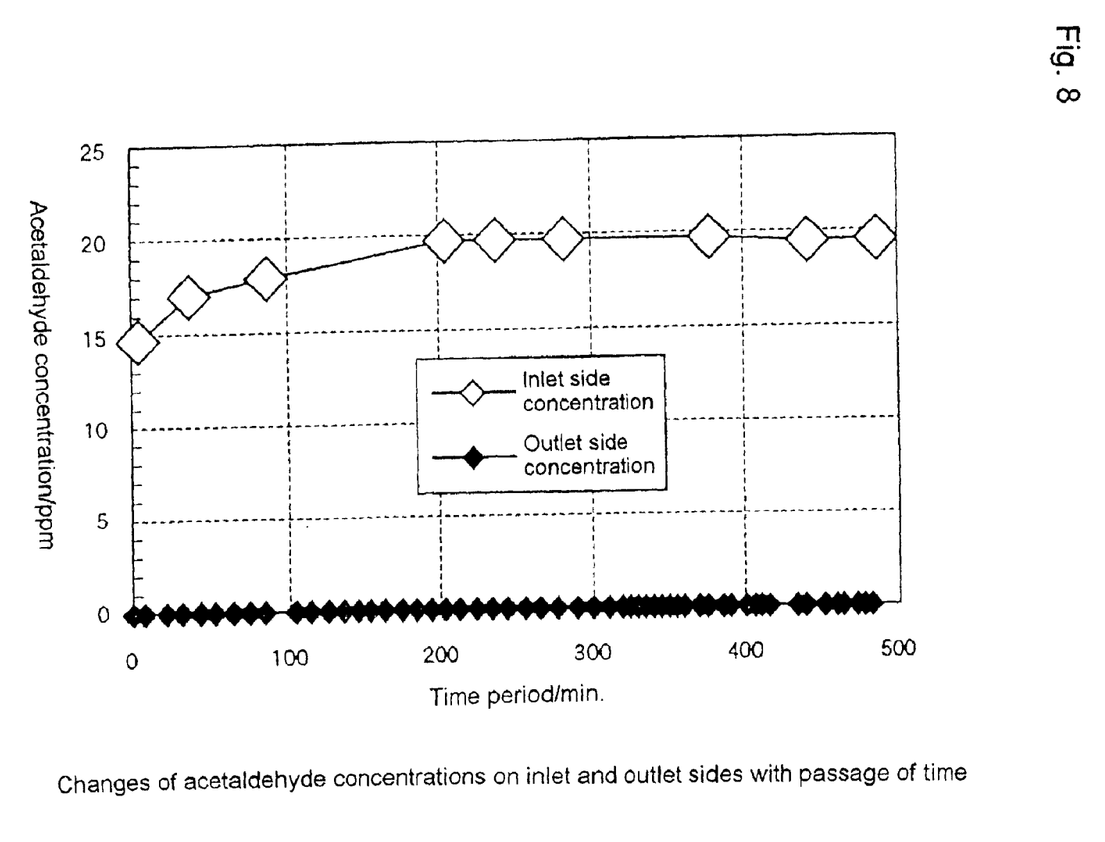
FIG. 8 is a graph showing concentrations of acetaldehyde on the inlet and the outlet of a filter when a gas containing 20 ppm of acetaldehyde was passed through a photocatalytic filter of the present invention.

FIG. 8 is a graph showing an inlet side concentration and an outlet side concentration of acetaldehyde when acetaldehyde having a concentration of approximately 20 ppm was flowed through a photocatalytic filter of the present invention. As shown in FIG. 8, when acetaldehyde having an inlet side concentration of approximately 20 ppm was flowed through the photocatalytic filter of the present invention, the outlet side concentration thereof decreased to a level of the detection limit value (0.08 ppm) of the detector or lower. Further, even when the gas was continuously flowed for approximately 500 minutes, the outlet side concentration showed a level of the detection limit value (0.08 ppm) of the detector or lower, so that it was found that the gas having an acetaldehyde concentration of approximately 20 ppm was decomposed and removed at one step to a concentration level of 1/100 or lower.

Figure 9:
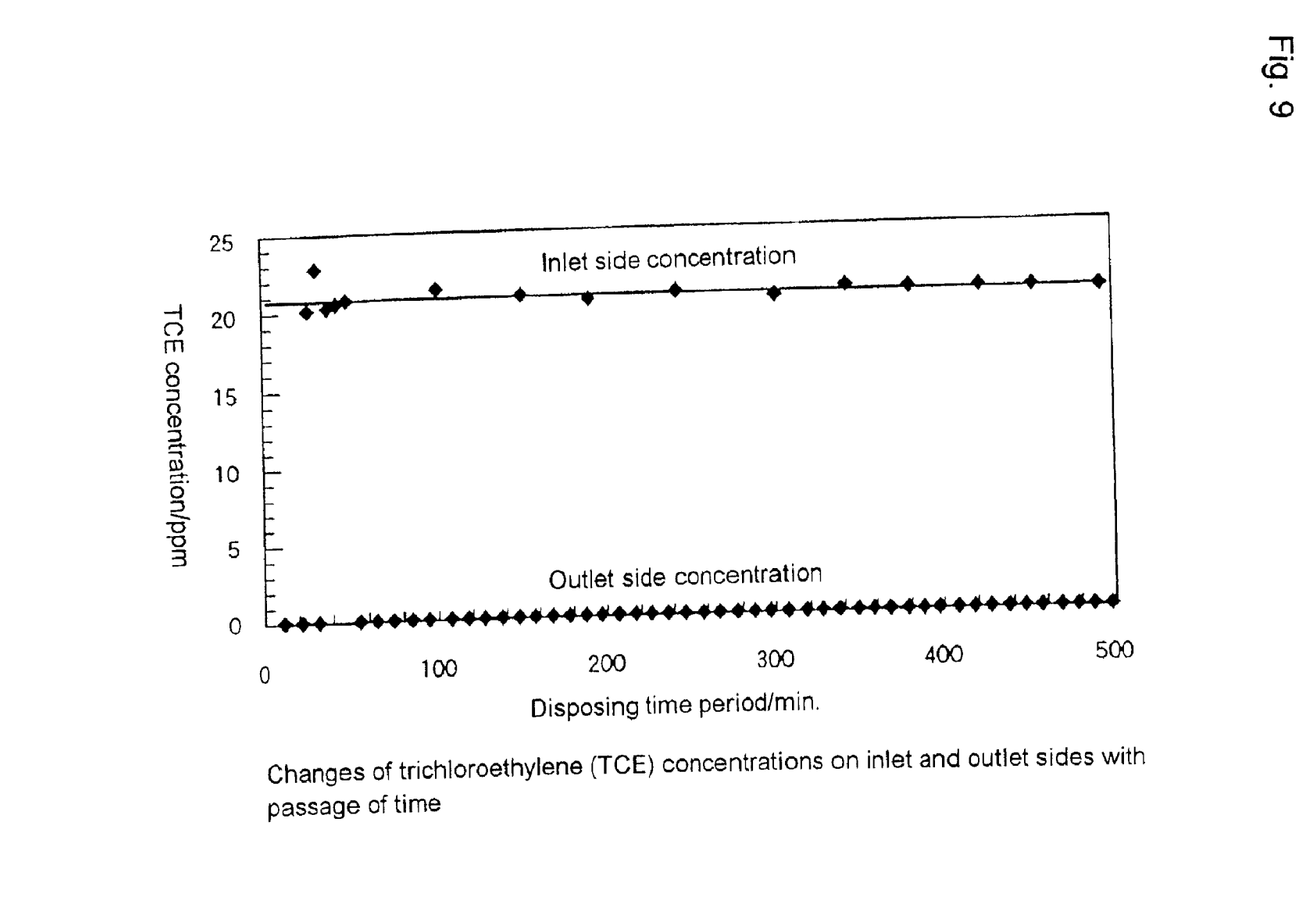
FIG. 9 is a graph showing concentrations of trichloroethylene on the inlet and the outlet of a filter when a gas containing 20 ppm of trichloroethylene was passed through a photocatalytic filter of the present invention.

FIG. 9 is a graph showing an inlet side concentration and an outlet side concentration of trichloroethylene when a gas having a trichloroethylene concentration of approximately 20 ppm was flowed through the photocatalytic filter of the present invention. As shown in FIG. 9, when the gas having an inlet side trichloroethylene concentration of approximately 20 ppm was flowed through the photocatalytic filter of the present invention, the outlet side trichloroethylene concentration thereof decreased to a level of the detection limit value (0.08 ppm) of the detector or lower. Further, even when the gas was continuously flowed for approximately 500 minutes, the outlet side trichloroethylene concentration showed a level of the detection limit value (0.08 ppm) of the detector or lower, so that it was found that the trichloroethylene having a concentration of approximately 20 ppm was decomposed and removed at one step to a concentration level of 1/100 or lower.

Figure 10:
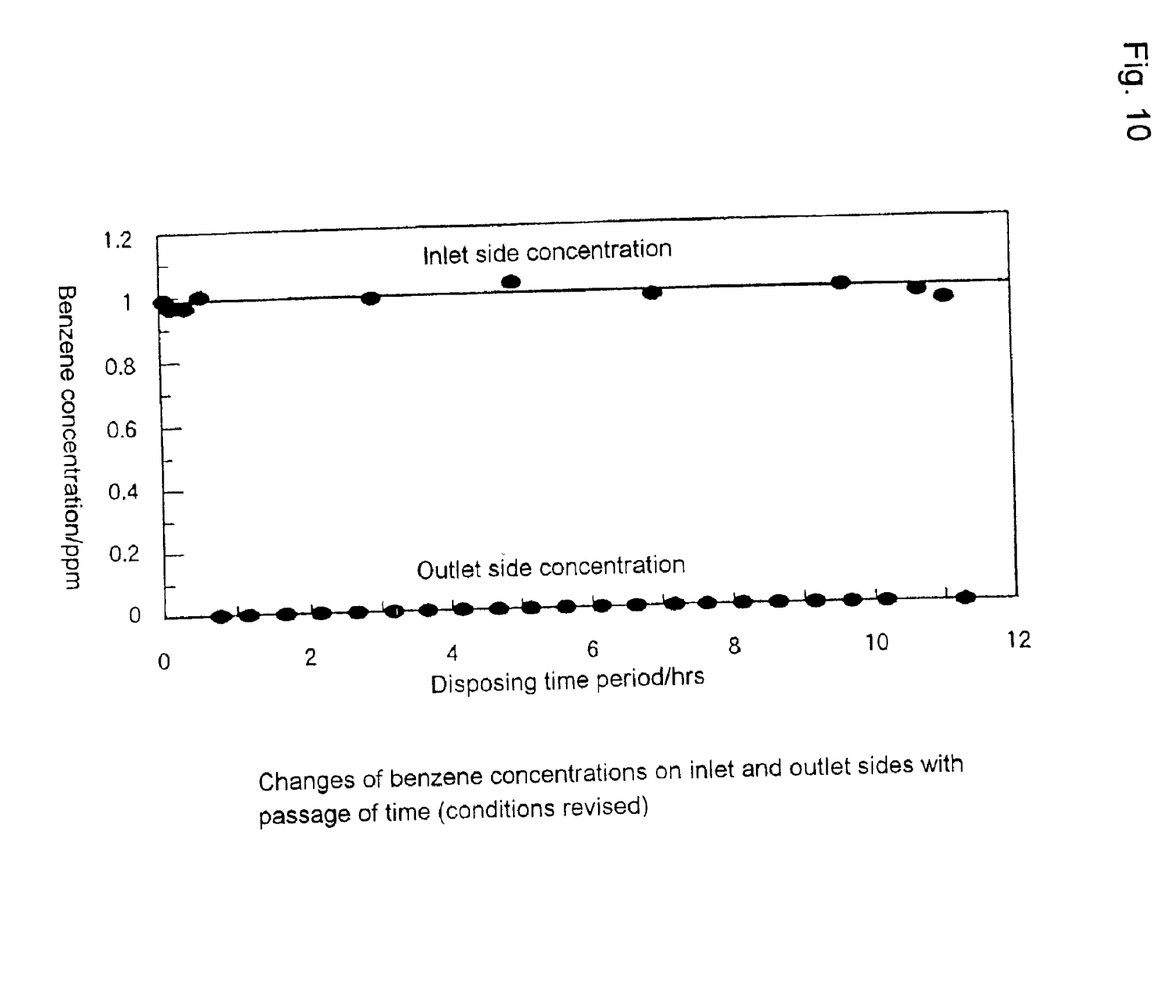
FIG. 10 is a graph showing concentrations of benzene on the inlet and the outlet of a filter when a gas containing 1 ppm of benzene was passed through a photocatalytic filter of the present invention.

FIG. 10 is a graph showing an inlet side concentration and an outlet side concentration of benzene when a gas having a benzene concentration of approximately 1 ppm was flowed through the photocatalytic filter of the present invention. By taking account of the very low concentration (approximately 1 ppm) of benzene, the intensity of ultraviolet ray (365 nm) to irradiate the photocatalytic filter was set at 20 mW/cm$^2$, the residence time of benzene in the photocatalytic filter was adjusted to 5.4 seconds, and the flow rate thereof was set at 1 liter/minute, to evaluate the photocatalytic filter. As shown in FIG. 10, when the gas having an inlet side benzene concentration of approximately 1 ppm was flowed through the photocatalytic filter of the present invention, the outlet side benzene concentration thereof decreased to a level of the detection limit value (0.08 ppm) of the detector or lower. Further, with regard to benzene which was presumably contained in air on the outlet side, the benzene was concentrated with TENAX (sampling tube) and subjected to quantitative analysis of a trace amount with a GC-MS analyzer (gas-chromatograph-mass-spectrometer), to show that the benzene was decomposed and removed to a level of the detection limit value of 0.2 ppb or lower.

What is claimed is:

1. A photocatalytic filter comprising a bundle of photocatalytic filter material,
    the photocatalytic filter material being formed of photoconductive particles, a photoconductive linear material and a photocatalyst layer,
    the particles being bonded to an outer surface of the linear material, each of said particles having a diameter smaller than a diameter of said linear material,
    the photocatalyst layer being formed on an outer surface of the linear material to which the particles are bonded, and on outer surfaces of the particles,
    the photocatalytic filter material being bundled for flowing a fluid to be disposed of, through gaps formed among adjacent portions of said photocatalytic filter material, to dispose of the fluid,
    said particles forming stacks each of which has a plurality of stages, said stacks being in the form of islands on the outer surface of the linear material.

2. The photocatalytic filter of claim 1, wherein said photoconductive linear material is a fiber made of a glass or a plastic, and said photoconductive particles are spheres made of a glass or a plastic.

3. A photocatalytic filter device using the photocatalytic filter of claim 1, the photocatalytic filter being housed in a filter case, the filter case having a flange portion on a side of a first end of the filter case and another flange portion on a side of a second end, the flange portion on the side of the first end being provided with an inlet port for introducing a fluid to be disposed of, the flange portion on the side of the second end being provided with an outlet port for discharging said fluid disposed of, one or each of the flange portions having a front side provided with a glass window for allowing light to enter a light incidence portion of said photocatalytic filter.

4. A method for manufacturing the photocatalytic filter of claim 1, the method comprising:

providing a predetermined number of photoconductive linear materials and a predetermined number of particles, and bonding said particles to surfaces of said linear materials and forming a photocatalyst layer on each of the linear materials to which the particles are bonded, the bonding step comprising:

temporarily bonding said particles to said linear materials while an adhesive liquid is interposed between the linear materials and the particles, and drying or curing said adhesive liquid while said linear materials are moved in a relative motion by applying accelerated motion based on shaking or rocking said linear materials to which the particles are temporarily bonded.

5. The method of claim 4, wherein said photoconductive linear material is a fiber made of a glass or a plastic, and said photoconductive particles are spheres made of a glass or a plastic.

* * * * *